(12) United States Patent
Hwang et al.

(10) Patent No.: US 7,671,236 B2
(45) Date of Patent: Mar. 2, 2010

(54) PROCESS FOR PRODUCTION OF CYCLOHEXANONE OXIME

(75) Inventors: Jih-Dar Hwang, Taipei (TW); Kai-Hung Haung, Taipei (TW); Hsiu-Li Cheng, Taipei (TW); Shou-Li Luo, Taipei (TW)

(73) Assignee: China Petrochemical Development Corporation, Taipei (TW)

( * ) Notice: Subject to any disclaimer, the term of this patent is extended or adjusted under 35 U.S.C. 154(b) by 0 days.

(21) Appl. No.: 11/986,366

(22) Filed: Nov. 20, 2007

(65) Prior Publication Data
US 2008/0167496 A1 Jul. 10, 2008

(30) Foreign Application Priority Data
Jan. 5, 2007 (TW) .............................. 96100436 A

(51) Int. Cl.
*C07C 249/08* (2006.01)
(52) U.S. Cl. .................. 564/259; 564/262; 564/264
(58) Field of Classification Search ...................... None
See application file for complete search history.

(56) References Cited

U.S. PATENT DOCUMENTS

| | | | | |
|---|---|---|---|---|
| 3,940,442 A | * | 2/1976 | de Rooij | 564/259 |
| 3,997,607 A | * | 12/1976 | de Rooij | 564/259 |
| 4,122,153 A | * | 10/1978 | Haasen et al. | 423/387 |
| 6,844,469 B2 | * | 1/2005 | Benneker et al. | 564/267 |
| 2004/0116745 A1 | * | 6/2004 | Blaauw et al. | 564/267 |
| 2008/0167495 A1 | * | 7/2008 | Hwang et al. | 564/259 |

OTHER PUBLICATIONS

Database CAPLUS on STN, Acc. No. 2005:505024, CN 1424306 (Jun. 18, 2003) (abstract).*

* cited by examiner

*Primary Examiner*—Brian J Davis
(74) *Attorney, Agent, or Firm*—Edwards Angell Palmer & Dodge LLP; Peter F. Corless; Dwight D. Kim

(57) ABSTRACT

Provided is a process of producing cyclohexanone oxime comprising the steps of: pre-mixing an inorganic process solution containing a high concentration of hydroxylamine phosphate with a first stream of cyclohexanone such that the concentration of hydroxylamine phosphate is reduced to 80% or less of its initial concentration; and subjecting hydroxylamine phosphate in the premixed inorganic process solution to an oximation reaction with a second stream of cyclohexanone. According to the process, oximation is performed after the inorganic process solution containing a high concentration of hydroxylamine phosphate has been pre-mixed with the first stream of cyclohexanone to reduce the concentration of hydroxylamine phosphate. As a result, not only that the efficiency of oximation and the yield of cyclohexanone oxime are increased, but also the organic content of the inorganic process solution discharged from the oximation tower is reduced.

13 Claims, 2 Drawing Sheets

PROCESS FOR PRODUCTION OF CYCLOHEXANONE OXIME

FIELD OF THE INVENTION

The present invention relates to processes of preparing cyclohexanone oxime, particularly, a process of preparing cyclohexanone oxime by using a high concentration of hydroxylamine phosphate and cyclohexanone.

BACKGROUND OF THE INVENTION

Cyclohexanone oxime is an important intermediate in the industrial production of caprolactam. Cyclohexanone oxime is typically produced by reacting cyclohexanone with hydroxylamine phosphate, and its production status will directly affect the production cost and yield of caprolactam.

FIG. 1 is a schematic diagram showing a conventional recycling system for hydroxylamine formation and oximation. As shown in FIG. 1, the conventional recycling system comprises a hydroxylamine formation tower (10), an oximation tower (30), an extraction tower (50), a stripping tower (70) and a nitric acid absorption tower (90). In the system, inorganic process solution containing nitrate ions and hydrogen gas are delivered, respectively, via lines 101 and 103 to the hydroxylamine formation tower (10), where hydroxylamine phosphate is synthesized. Unreacted hydrogen gas and other gases formed are discharged via a line 105. The inorganic process solution containing hydroxylamine phosphate is delivered via a line 111 to the oximation tower (30) by feeding from the top, and an organic phase solution containing cyclohexanone is delivered via lines 113 and 115 to the bottom of the oximation tower (30). The two solutions feeding from the opposite directions contacted with each other to carry out oximation reaction. The organic phase containing the produced cyclohexanone oxime is discharged to the top of the oximation tower (30) via a line 117, while the residual phosphate-containing inorganic process solution is discharged from the bottom of the oximation tower (30) via a line 119. The discharged phosphate-containing inorganic process solution is delivered via the line 119 to the extraction tower (50), where the residual cyclohexanone oxime is removed; then, the phosphate-containing inorganic process solution is delivered via a line 125 to the stripping tower (70), where the phosphate-containing inorganic process solution is stripped to further remove the residual organic impurities. Finally, the stripped phosphate-containing inorganic process solution is delivered via a line 127 to the nitric acid absorption tower (90), where the inorganic process solution is supplemented with nitrate ions, and then the phosphate-containing inorganic process solution is recycled to the hydroxylamine formation tower (10) for use in hydroxylamine phosphate synthesis in the next cycle.

However, the conventional recycling system has a problem, namely, it is difficult to enhance the yield per unit time, if the design of the oximation tower remains unchanged. For example, when the inorganic process solution containing hydroxylamine phosphate and the organic solution containing cyclohexanone are fed into the oximation tower in an increased amount and/or an increased concentration of hydroxylamine and cyclohexanone contained therein, when the yield of cyclohexanone oxime per unit time is increased, the efficiency of oximation may decrease if the oximation tower is overloaded. As a result, the yield cannot be effectively increased. To overcome the above problem, one can increase the number or the volume of the oximation tower or change the mode of operation. However, the former is limited by the production cost and compliance with regulations (installment of a new oximation tower is expensive; the height of the original equipment cannot be unlimitedly increased); and the latter may cause problems in the way of feeding. For example, as disclosed Chinese patent publication No. 1424306, an oximation process with high efficiency, wherein the solution of cyclohexanone was fed into the oximation tower in a reduced amount from the bottom of the oximation tower, while it was fed in an increased amount from the meddle part of the oximation tower, thereby lowering the organic compounds (including cyclohexanone and cyclohexanone oxime) in the phosphate-containing inorganic process solution discharged from the bottom of the oximation tower. However, in case that the concentration or the flow rate of the inorganic process solution containing hydroxylamine phosphate fed into the oximation tower and/or the concentration of the hydroxylamine phosphate therein are greatly increased, changes in the position where the cyclohexanone stream is fed may result in incomplete oximation, which would lead to increasing in the total carbonyl content of the phosphate-containing inorganic process solution discharged from the bottom of oximation tower, and in turn, inactivate the catalyst in the hydroxylamine formation tower.

Accordingly, it is necessary to develop a process for producing cyclohexanone oxime, which not only provides enhanced efficiency of oximation and increase yield of cyclohexanone oxime, but also lowers the organic content in the inorganic process solution discharged from the oximation tower, even if the amount of feeds for the oximation tower and/or the concentration of hydroxylamine phosphate in the feed are greatly increased.

SUMMARY OF THE INVENTION

It is therefore an objective of the invention to provide a process of producing cyclohexanone oxime by using a feed containing a high concentration of hydroxylamine phosphate.

It is another objective of the invention to provide a process of producing cyclohexanone oxime, and the process can increase efficiency of oximation and yield of cyclohexanone oxime.

It is yet another objective of the invention to provide a process of producing cyclohexanone oxime, and the process can lower the organic content in the inorganic process solution discharged from the oximation tower.

In accordance with the foregoing and other objectives, the invention proposes a process of producing cyclohexanone oxime, comprising the following steps: (a) pre-mixing an inorganic process solution containing a high concentration of hydroxylamine phosphate with a first stream of cyclohexanone in such a manner that the concentration of hydroxylamine phosphate is reduced to 80% or less of its initial concentration; and (b) subjecting hydroxylamine phosphate in the pre-mixed inorganic process solution to an oximation reaction with a second stream of cyclohexanone.

According to the process of the invention, oximation is performed after the inorganic process solution containing a high concentration of hydroxylamine phosphate is pre-mixed with some cyclohexanone to reduce the concentration of hydroxylamine phosphate, thereby increasing the efficiency of oximation and reducing the organic content of the inorganic process solution discharged from the oximation tower.

BRIEF DESCRIPTION OF DRAWINGS

The invention can be more fully understood by reading the following detailed description of the preferred embodiments, with reference made to the accompanying drawings, wherein.

DETAILED DESCRIPTION OF THE INVENTION

The term "total carbonyl content" herein refers to the weight ratio of both of cyclohexanone and cyclohexanone oxime, based on the total weight of the inorganic process solution.

The process according to the invention can be applied to a recycling system for hydroxylamine formation and oximation. In the system, phosphate-containing inorganic process solution is used as the aqueous reaction medium throughout the entire cycle. First, hydroxylamine phosphate is synthesized in a hydroxylamine formation tower by reducing nitrate with a hydrogen gas. Then, hydroxylamine phosphate is premixed with a first stream of cyclohexanone in a pre-mixing tank to lower the concentration of hydroxylamine phosphate in the feed. The pre-mixed reaction mixture is then delivered to an oximation tower, where hydroxylamine phosphate is subjected to an oximation reaction to form cyclohexanone oxime. The phosphate-containing inorganic process solution, discharged from the oximation tower after removing organic impurities and supplementing nitrate ions, is recycled back to the hydroxylamine formation tower for use in the next cycle of reactions.

Figure 1:
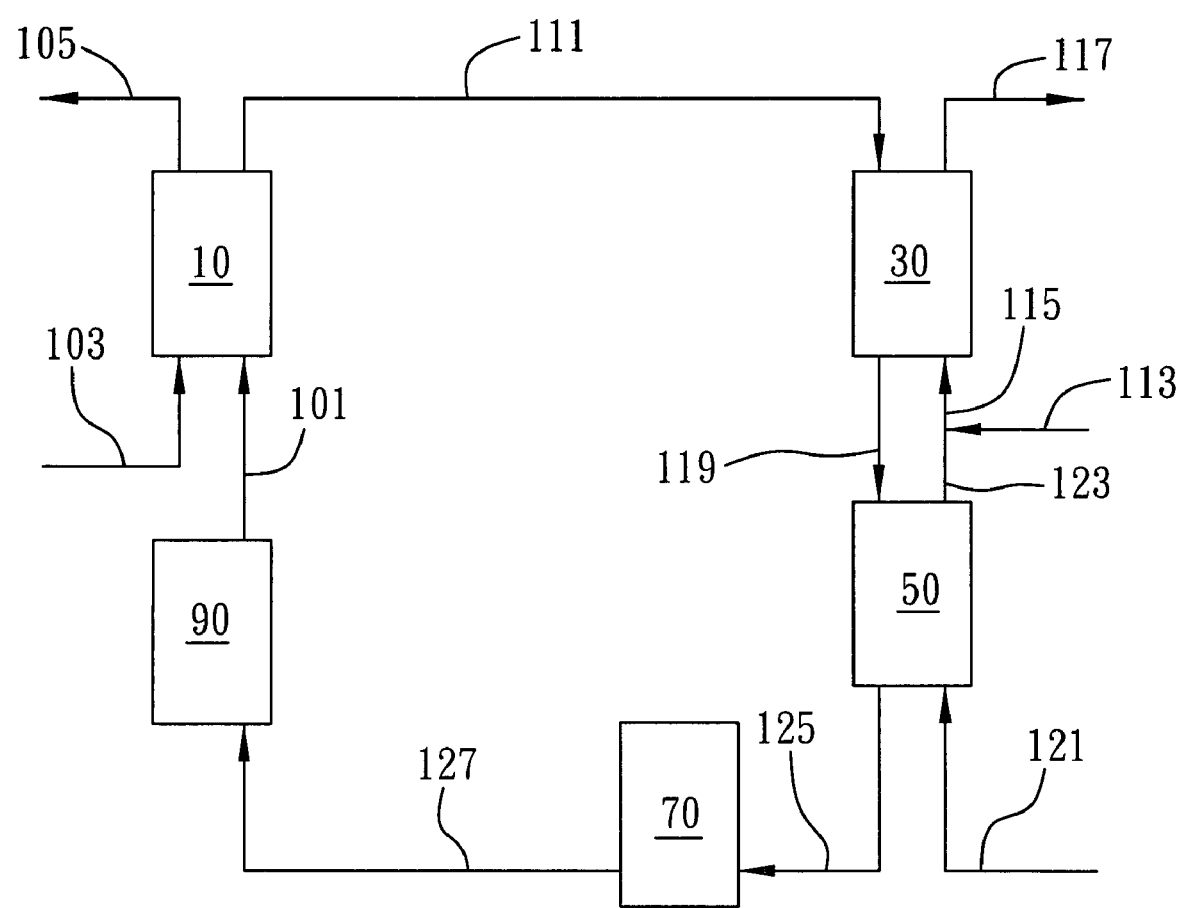
FIG. 1 is a schematic diagram of a conventional recycling system of hydroxylamine formation and oximation.
Figure 2:
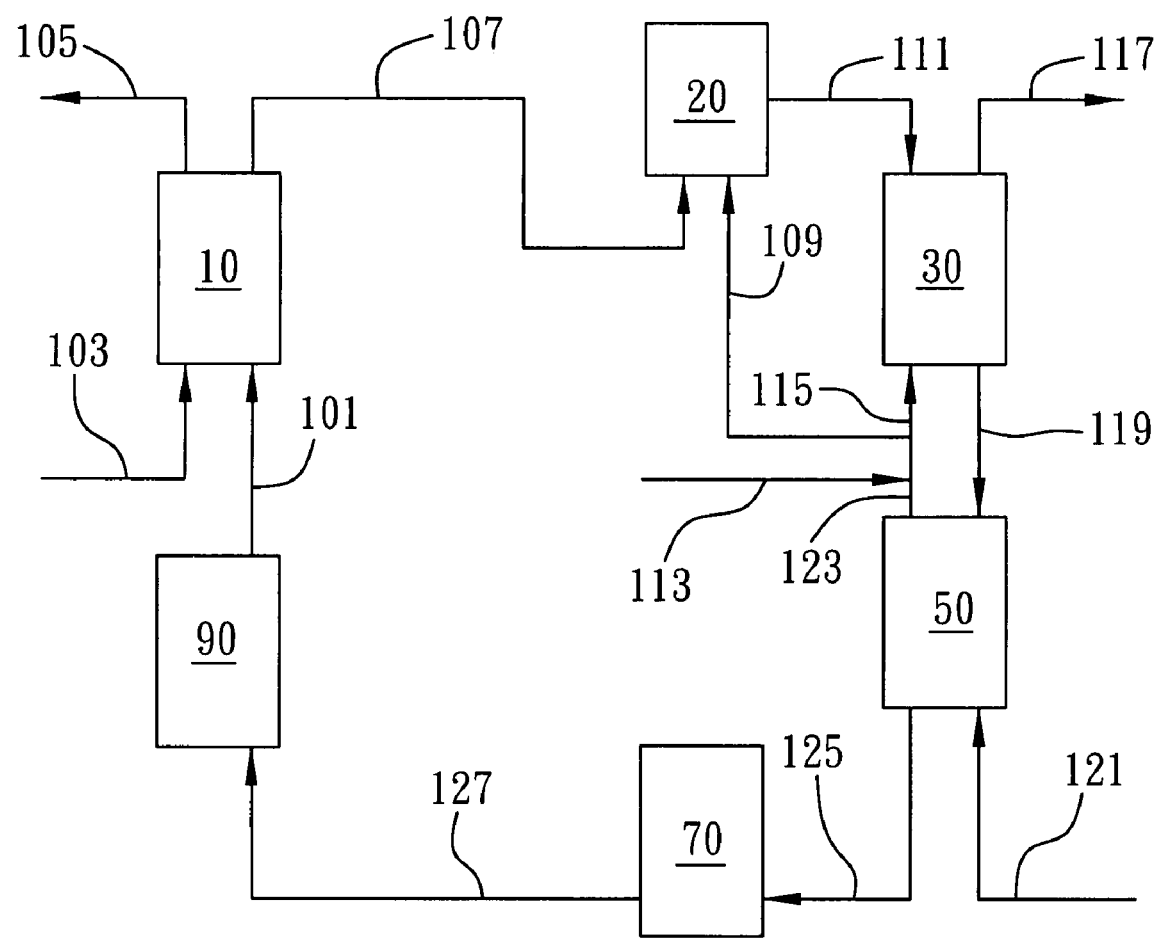
FIG. 2 is a simplified schematic figure of the recycling system for hydroxylamine formation and oximation according to the invention.

As shown in FIG. 2, in this embodiment, the system for hydroxylamine formation and oximation, which is suitable for use in the process of the invention, comprises a hydroxylamine formation tower (10), pre-mixing tank (20), an oximation tower (30), an extraction tower (50), a stripping tower (70) and a nitric acid absorption tower (90). According to the invention, the inorganic process solution containing nitrate ions and hydrogen gas are delivered, respectively, via lines 101 and 103 to the hydroxylamine formation tower (10), where a high concentration of hydroxylamine phosphate is obtained. Unreacted hydrogen gas and other gases formed are discharged via a line 105. The term "high concentration of hydroxylamine phosphate" herein means that the concentration of hydroxylamine phosphate in the inorganic process solution is 1.0 mol/kg or more, preferably 1.2 mol/kg or more, more preferably 1.4 mol/kg or more, and most preferably 1.6 mol/kg or more. The resulting inorganic process solution containing a high concentration of hydroxylamine phosphate and an organic phase solution containing cyclohexanone are delivered in the same direction to a pre-mixing tank (20), respectively, via lines 107 and 109, and both are pre-mixed at a temperature of 30 to 50° C. to form a pre-mixed reaction mixture. The concentration of hydroxylamine phosphate in the pre-mixed reaction mixture has decreased to 80% or less, preferably 70% or less, more preferably 60% or less, especially preferably 50% or less, of its initial concentration. The cyclohexanone-containing organic phase solution comprises cyclohexanone and an organic solvent. Examples of the organic solvent include, but not limited to, benzene, toluene, xylene, methylcyclopentane, cylcohexane and the mixtures thereof.

The pre-mixed reaction mixture is delivered via a line 111 to the top of the oximation tower (30), and the cyclohexanone-containing organic phase solution is delivered via lines 113 and 115 to the bottom of the oximation tower (30). Both, in the opposite flowing directions, contacted with each other and subjected to an oximation reaction. The oximation reaction is preferably performed at a temperature of 40 to 60° C. and under atmospheric, subatmospheric or superatmospheric pressure. The cyclohexanone-containing organic phase solution comprises cyclohexanone and an organic solvent. The examples of the organic solvent include, but not limited to, benzene, toluene, xylene, methylcyclopentane, cylcohexane and the mixtures thereof. After completion of oximation, the cyclohexanone-containing organic phase solution is discharged from the top of the oximation tower (30) via a line 117, while the residual phosphate-containing inorganic process solution is discharged from the bottom of the oximation tower (30) via a line 119.

The phosphate-containing inorganic process solution discharged from the bottom of the oximation tower (30) is delivered via a line 119 to the extraction tower (50). Toluene, which is used as the extraction solvent, is delivered via a line 121 to the extraction tower (50), where the phosphate-containing inorganic process solution is extracted with toluene to remove the residual cyclohexanone oxime. After extraction, the organic solvent is delivered back to the oximation tower (30) via a line 123, and the phosphate-containing inorganic process solution is discharged from the bottom of the extraction tower (50) and delivered via a line 125 to the stripping tower (70), where the phosphate-containing inorganic process solution is stripped to remove the residual organic impurities. The stripped inorganic process solution is delivered via a line 127 to the nitric acid absorption tower (90), where the inorganic process solution is supplemented with nitrate ions. Then, the phosphate-containing inorganic process solution is recycled to the hydroxylamine formation tower for use in hydroxylamine phosphate synthesis in the next cycle.

EXAMPLE

Control Example

Inorganic process solution containing hydroxylamine phosphate (with a concentration per unit time: 1.131 mol/kg) and a solution of cyclohexanone in toluene were continuously fed to an oximation tower, respectively, from the top and the bottom of the oximation tower to perform oximation at a temperature of 51° C., wherein the molar ratio of hydroxylamine to cyclohexanone was 0.90:1. In the organic phase discharged from the top of the oximation tower per unit time, there was 1.176 mol (132.9 g) of cyclohexanone oxime. In the phosphate-containing inorganic process solution discharged from the bottom of the oximation tower, the concentration of the unreacted hydroxylamine was below 0.001 mol/kg (calculated by the free form) and the total carbonyl content was 0.95 wt %.

Comparative Example 1

An Increased Concentration of Hydroxylamine in the Feed

The steps of the control example were repeated, except that the concentration of hydroxylamine phosphate fed to the oximation tower was 1.407 mol/kg and the concentration of cyclohexanone in the toluene solution was adjusted such that the molar ratio of hydroxylamine to cyclohexanone was 0.90:1. In the organic phase discharged from the top of the oximation tower per unit time, there was 1.158 mol (130.9 g) of cyclohexanone oxime. In the phosphate-containing inorganic process solution discharged from the bottom of the oximation tower, the concentration of the unreacted hydroxylamine phosphate was below 0.115 mol/kg (calculated by the free form) and the total carbonyl content was 1.60 wt %.

By comparing with Control Example, Comparative Example 1 showed that by increasing the concentration of hydroxylamine in the feed and loading of the oximation tower, incomplete oximation had resulted, which led to an increased total carbonyl content in the phosphate-containing inorganic process solution discharged from the bottom of the oximation tower.

Example 1

The procedures of Comparative Example were repeated, except that the inorganic process solution containing hydroxylamine phosphate and the first part of the solution of cyclohexanone in toluene were delivered in the same direction to a pre-mixing tank, where both solutions were pre-mixed at a temperature of 37° C. and under atmospheric pressure. The concentration of hydroxylamine phosphate in the reaction mixture discharged from the pre-mixing tank was reduced to 45% of its initial concentration.

The pre-mixed reaction mixture was fed to the oximation tower from its top, while and the second part of the solution of cyclohexanone in toluene was fed to the oximation tower from its bottom. Both feeds delivered from the opposite directions contacted with each other at a temperature of 51° C. and subjected to an oximation reaction, wherein the molar ratio of hydroxylamine to total cyclohexanone of the two parts was 0.90:1. In the organic phase discharged from the top of the oximation tower per unit time, there was 1.434 mol (162.0 g) of cyclohexanone oxime. In the phosphate-containing inorganic process solution discharged from the bottom of the oximation tower, the concentration of the unreacted hydroxylamine was below 0.001 mol/kg (calculated by the free form) and the total carbonyl content was 1.20 wt %.

By comparing with Comparative Example 1, Example 1 showed that by performing oximation after the concentration of hydroxylamine phosphate in the inorganic process solution was decreased by pre-mixing a high concentration of hydroxylamine phosphate with a part of cyclohexanone in the pre-mixing tank. This not only increased the efficiency of oximation, but also reduced the discharge of the organic content of the inorganic process solution from the oximation tower.

Comparative Example 2

The procedures of the control example were repeated, except that the concentration of hydroxylamine phosphate in the inorganic process solution fed to the oximation tower was 1.642 mol/kg and the molar ratio of hydroxylamine to cyclohexanone was 0.90:1. In the organic phase discharged from the top of the oximation tower per unit time, there was 1.404 mol (158.65 g) of cyclohexanone oxime. In the inorganic process solution discharged from the bottom of the oximation tower, the concentration of the unreacted hydroxylamine was 0.131 mol/kg (calculated by the free form) and the total carbonyl content was 2.01 wt %.

By comparing with Control example, Comparative Example 2 showed that by increasing the concentration of hydroxylamine in the feed, an increase in loading of the oximation tower had resulted, which would lead to incomplete oximation.

Example 2

The procedures of Comparative Example 2 were repeated, except that the inorganic process solution containing hydroxylamine phosphate and a first part of the solution of cyclohexanone in toluene were fed in the same direction to a pre-mixing tank, where both solutions were pre-mixed at a temperature of 37° C. and under atmospheric pressure. The concentration of hydroxylamine phosphate in the reaction mixture discharged from the pre-mixing tank was reduced to 63% of its initial concentration.

The pre-mixed reaction mixture was fed to the top of the oximation tower, while the other part of cyclohexanone in toluene was fed to the bottom of the oximation tower. Both feeds delivered from the opposite directions contacted with each other at a temperature of 51° C. and subjected to an oximation reaction, wherein the molar ratio of hydroxylamine to total cyclohexanone of the two parts was 0.90:1. In the organic phase discharged from the top of the oximation tower per unit time, there was 1.614 mol (182.4 g) of cyclohexanone oxime. In the phosphate-containing inorganic process solution discharged from the bottom of the oximation tower, the concentration of the unreacted hydroxylamine was below 0.001 mol/kg (calculated by the free form) and the total carbonyl content was 1.65 wt %.

By comparing with Comparative Example 2, Example 2 showed that by performing oximation after the concentration of hydroxylamine phosphate in the inorganic process solution decreased by pre-mixing the inorganic process solution containing a high concentration of hydroxylamine phosphate with some cyclohexanone in the pre-mixing tank. This not only increased the efficiency of oximation, but also reduced the discharge of the organic content of the inorganic process solution from the oximation tower.

Comparative Example 3

An Increased Amount of Feeds

The procedures of the control example were repeated, except that the amount of the inorganic process solution containing hydroxylamine phosphate fed to the oximation tower per unit time was increased by 1.18 times, as compared with Control Example. The amount of the solution of cyclohexanone in toluene was increased in the same proportion such that the molar ratio of hydroxylamine to cyclohexanone was 0.90:1. In the organic phase discharged from the top of the oximation tower per unit time, there was 1.047 mol (121.4 g) of cyclohexanone oxime. In the phosphate-containing inorganic process solution discharged from the bottom of the oximation tower, the concentration of the unreacted hydroxylamine was 0.095 mol/kg (calculated by the free form) and the total carbonyl content was 1.55 wt %.

By comparing with Control Example, Comparative Example 3 showed that by increasing the amount of the feed, increased loading of the oximation tower had resulted, which led to incomplete oximation. As a result, the total carbonyl content in the inorganic process solution discharged from the bottom of the oximation tower was increased.

Example 3

The procedures of Comparative Example 3 were repeated except the inorganic process solution containing hydroxylamine phosphate and a first part of the solution of cyclohexanone in toluene were fed in the same direction to a pre-mixing tank, where both solutions were pre-mixed at a temperature of 37° C. and under atmospheric pressure. The concentration of hydroxylamine phosphate in the reaction mixture discharged from the pre-mixing tank was reduced to 59% of its initial concentration.

The pre-mixed reaction mixture was fed to the top of the oximation tower and a second part of the solution of cyclohexanone in toluene was fed to the oximation tower from the bottom of the oximation tower. Both feeds delivered from the opposite directions contacted with each other at a temperature of 51° C. and subjected to an oximation reaction, wherein the molar ratio of hydroxylamine to total cyclohexanone of the two parts was 0.90:1. In the organic phase discharged from the top of the oximation tower per unit time, there was 1.386 mol (156.6 g) of cyclohexanone oxime. In the phosphate-containing inorganic process solution discharged from the bottom of the oximation tower, the concentration of the unreacted hydroxylamine was below 0.001 mol/kg (calculated by the free form) and the total carbonyl content was 1.20 wt %.

By comparing with Comparative Example 3, Example 3 showed that the disadvantage of incomplete oximation caused by increased loading of the oximation tower due to increased amount of the feed can be overcome by pre-mixing the inorganic process solution containing a high concentration of hydroxylamine phosphate with a part of the solution of cyclohexanone in toluene.

Comparative Example 4

An Increased Amount of Feeds and Elevated Concentration of Hydroxylamine Phosphate Therein The procedures of Comparative Example 3 were repeated, except that the concentration of hydroxylamine phosphate in the inorganic process solution fed to the oximation tower was 1.407 mol/kg and the molar ratio of hydroxylamine to cyclohexanone was 0.90:1. In the organic phase discharged from the top of the oximation tower, there was 1.302 mol (147.1 g) of cyclohexanone oxime. In the phosphate-containing inorganic process solution discharged from the bottom of the oximation tower, the concentration of the unreacted hydroxylamine was 0.120 mol/kg (calculated by the free form) and the total carbonyl content was 1.64 wt %.

By comparing with Control example, Comparative Example 4 showed that by increasing the amount of the feed and increasing the concentration of hydroxylamine phosphate therein, increased loading of the oximation tower had resulted, which led to incomplete oximation. In turn, increased the total carbonyl content in the phosphate-containing inorganic process solution discharged from the bottom of the oximation tower.

Example 4

The procedures of Comparative Example 4 were repeated, except that the inorganic process solution containing hydroxylamine phosphate and a first part of the solution of cyclohexanone in toluene were fed in the same direction to a pre-mixing tank, where both solutions were pre-mixed at a temperature of 37° C. and under atmospheric pressure. The concentration of hydroxylamine phosphate in the reaction mixture discharged from the pre-mixing tank was reduced to 72% of its initial concentration.

The pre-mixed reaction mixture was fed to the top of the oximation tower and a second part of the solution of cyclohexanone in toluene was fed from the bottom of the oximation tower. Both feeds delivered from the opposite directions contacted with each other at a temperature of 51° C. and subjected to an oximation reaction, wherein the molar ratio of hydroxylamine to total cyclohexanone of the two parts was 0.90:1. In the organic phase discharged from the top of the oximation tower, there was 1.716 mol (193.9 g) of cyclohexanone oxime. In the phosphate-containing inorganic process solution discharged from the bottom of the oximation tower, the concentration of the unreacted hydroxylamine was below 0.001 mol/kg (calculated by the free form) and the total carbonyl content was 1.40 wt %.

By comparing with Comparative Example 4, Example 4 showed that the disadvantage of incomplete oximation caused by increased loading of the oximation tower due to an increased amount of the feeds and an increased concentration hydroxylamine phosphate therein, can be overcome by pre-mixing the inorganic process solution containing hydroxylamine phosphate with a part of the solution of cyclohexanone in toluene.

According to the invention, the efficiency of oximation can be increased and the organic content of the inorganic process solution discharged from the oximation tower can be reduced in case that cyclohexanone oxime is produced by using a feed containing a high concentration of hydroxylamine phosphate.

The invention has been described using exemplary preferred embodiments. However, it is to be understood that the scope of the invention is not limited to the disclosed embodiments. On the contrary, it is intended to cover various modifications and similar arrangements. The scope of the claims, therefore, should be accorded the broadest interpretation so as to encompass all such modifications and similar arrangements.

What is claimed is:

1. A process of producing cyclohexanone oxime, comprising the following steps:
    (a) pre-mixing an inorganic process solution containing a predetermined concentration of hydroxylamine phosphate with a first stream of cyclohexanone such that the concentration of hydroxylamine phosphate is reduced to 80% or less of its initial concentration; and
    (b) subjecting hydroxylamine phosphate in the pre-mixed inorganic process solution to an oximation reaction with a second stream of cyclohexanone.

2. The process according to claim 1, wherein the predetermined concentration of hydroxylamine phosphate in the inorganic process solution in the step (a) is 1.0 mole/kg or more.

3. The process according to claim 2, wherein the predetermined concentration of hydroxylamine phosphate in the inorganic process solution in the step (a) is 1.2 mole/kg or more.

4. The process according to claim 3, wherein the predetermined concentration of hydroxylamine phosphate in the inorganic process solution in the step (a) is 1.6 mole/kg or more.

5. The process according to claim 1, wherein the step (a) is performed at a temperature of 30 to 50° C.

6. The process according to claim 1, wherein the pre-mixing in the step (a) is performed in a pre-mixing tank.

7. The process according to claim 6, wherein the first stream of cyclohexanone and the inorganic process solution containing a predetermined concentration of hydroxylamine phosphate are fed to the pre-mixing tank in the same direction.

8. The process according to claim 1, wherein the concentration of hydroxylamine phosphate in the inorganic process solution is reduced to 70% or less of its initial concentration after completion of the step (a).

9. The process according to claim 8, wherein the concentration of hydroxylamine phosphate in the inorganic process solution is reduced to 60% or less of its initial concentration after completion of the step (a).

10. The process according to claim 9, wherein the concentration of hydroxylamine phosphate in the inorganic process solution is reduced to 50% or less of its initial concentration after completion of the step (a).

11. The process according to claim 1, wherein the oximation reaction in the step (b) is performed in an oximation tower.

12. The process according to claim 11, wherein the premixed inorganic process solution is fed to the top of the oximation tower.

13. The process according to claim 1, wherein the first stream of cyclohexanone and the second stream of cyclohexanone are organic phases comprising cyclohexanone and an organic solvent.

* * * * *